US012653603B2

(12) United States Patent
Kerr et al.

(10) Patent No.: US 12,653,603 B2
(45) Date of Patent: Jun. 16, 2026

(54) SURGICAL INSTRUMENTS, SYSTEMS, METHODS, AND ATTACHMENTS THEREFOR UTILIZING VIBRATION FEEDBACK

(71) Applicant: Covidien LP, Mansfield, MA (US)

(72) Inventors: Duane E. Kerr, Loveland, CO (US); Christopher K. Gibbs, San Clemente, CA (US); Michelle P. Romero, Broomfield, CO (US); Michael A. Mercer, Castle Rock, CO (US); Brett C. Walker, Portland, OR (US); Lucas M. Lastoczy, Boulder, CO (US); Cameron P. Mahoney, Highlands Ranch, CO (US)

(73) Assignee: Covidien LP, Mansfield, MA (US)

( * ) Notice: Subject to any disclaimer, the term of this patent is extended or adjusted under 35 U.S.C. 154(b) by 289 days.

(21) Appl. No.: 18/553,971

(22) PCT Filed: Apr. 5, 2022

(86) PCT No.: PCT/US2022/023449
§ 371 (c)(1),
(2) Date: Oct. 4, 2023

(87) PCT Pub. No.: WO2022/216685
PCT Pub. Date: Oct. 13, 2022

(65) Prior Publication Data
US 2024/0180608 A1     Jun. 6, 2024

Related U.S. Application Data

(60) Provisional application No. 63/172,577, filed on Apr. 8, 2021.

(51) Int. Cl.
A61B 18/12     (2006.01)
A61B 18/14     (2006.01)
A61B 18/00     (2006.01)

(52) U.S. Cl.
CPC ...... *A61B 18/1445* (2013.01); *A61B 18/1206* (2013.01); *A61B 2018/0088* (2013.01)

(58) Field of Classification Search
CPC ............ A61B 18/1206; A61B 18/1445; A61B 18/148; A61B 2018/00601;
(Continued)

(56) References Cited

U.S. PATENT DOCUMENTS

2004/0186465 A1     9/2004  Francischelli et al.
2017/0181789 A1*    6/2017  Ding .................. A61B 18/1445
(Continued)

OTHER PUBLICATIONS

International Search Report and Written Opinion issued in corresponding International Application No. PCT/US2022/023449 mailed Jul. 18, 2022, 13 pages.

*Primary Examiner* — Daniel W Fowler

(57) ABSTRACT

A surgical system includes a surgical instrument, a motion sensor, and a computing device. The surgical instrument includes a housing, an end effector assembly distally-spaced from the housing, and a movable component movable relative to the housing. The motion sensor is disposed on or within the housing and configured to sense a vibration signature associated with movement of the movable component relative to the housing. The computing device communicates with the motion sensor, is configured to receive the vibration signature therefrom, and is configured to determine a condition of the movable component based on the vibration signature. A method of monitoring a surgical instrument includes sensing a vibration signature generated from movement of a movable component of a surgical instrument relative to a housing of the surgical instrument, (Continued)

and determining, based on the sensed vibration signature, a condition of the movable component.

18 Claims, 12 Drawing Sheets

(58) Field of Classification Search
CPC .. A61B 2018/00607; A61B 2018/0063; A61B 2018/0088; A61B 2018/1452; A61B 2018/1455; A61B 34/35; A61B 34/37
See application file for complete search history.

(56)                    References Cited

U.S. PATENT DOCUMENTS

| 2017/0252095 | A1* | 9/2017 | Johnson | ............. A61B 18/1445 |
|---|---|---|---|---|
| 2018/0071047 | A1* | 3/2018 | Suzuki | ................... A61B 34/20 |
| 2019/0201027 | A1* | 7/2019 | Shelton, IV | ........... A61B 5/065 |
| 2020/0138473 | A1 | 5/2020 | Shelton, IV et al. | |
| 2020/0405405 | A1 | 12/2020 | Shelton, IV et al. | |

* cited by examiner

SURGICAL INSTRUMENTS, SYSTEMS, METHODS, AND ATTACHMENTS THEREFOR UTILIZING VIBRATION FEEDBACK

CROSS-REFERENCE TO RELATED APPLICATION

This application is a 371 National Stage Application of International Application No. PCT/US2022/023449, filed Apr. 5, 2022, which claims the benefit of, and priority to, U.S. Provisional Patent Application No. 63/172,577, filed on Apr. 8, 2021, the entire contents of which is hereby incorporated herein by reference.

FIELD

The present disclosure relates to surgical instruments, systems, methods, and attachments therefor utilizing vibration feedback, e.g., to determine a position, orientation, speed, or other condition of a component.

BACKGROUND

Surgical instruments, systems, and methods typically utilize mechanical action of one or more jaw members and/or other components to facilitate grasping, manipulating, and/or treating tissue. Some of such instruments, systems, and methods utilize purely mechanical action, e.g., surgical graspers, surgical clip applies, surgical staplers, etc., while others utilize mechanical action, e.g., grasping tissue, penetrating tissue, deploying component(s) relative to tissue, etc., to facilitate energy-based tissue treatment, e.g., using Radio Frequency (RF) energy, ultrasonic energy, thermal energy, microwave energy, light energy, etc.

SUMMARY

As used herein, the term "distal" refers to the portion that is being described which is farther from an operator (whether a human surgeon or a surgical robot), while the term "proximal" refers to the portion that is being described which is closer to the operator. Terms including "generally," "about," "substantially," and the like, as utilized herein, are meant to encompass variations, e.g., manufacturing tolerances, material tolerances, use and environmental tolerances, measurement variations, and/or other variations, up to and including plus or minus 10 percent. Further, any or all of the aspects described herein, to the extent consistent, may be used in conjunction with any or all of the other aspects described herein.

Provided in accordance with aspects of the present disclosure is a surgical system including a surgical instrument, a motion sensor, and a computing device. The surgical instrument includes a housing, an end effector assembly distally-spaced from the housing, and a movable component movable relative to the housing upon actuation of the movable component. The motion sensor is disposed on or within the housing (e.g., on or within the body portion thereof, the fixed handle portion thereof, or on or within another component such as, for example, the movable handle) and configured to sense a vibration signature associated with movement of the movable component relative to the housing. The computing device communicates with the motion sensor, is configured to receive the vibration signature therefrom, and is configured to determine a condition of the movable component based on the vibration signature.

In an aspect of the present disclosure, the surgical instrument further includes an amplification mechanism coupled to the movable component and configured to produce amplified vibrations to facilitate sensing the vibration signature. The amplification mechanism may include a discrete amplifier and/or a continuous amplifier.

In another aspect of the present disclosure, the condition of the movable component includes at least one of: an amount of movement of the movable component, a direction of movement of the movable component, a speed of movement of the movable component, or an acceleration of movement of the movable component.

In yet another aspect of the present disclosure, the movable component is configured to translate relative to the housing upon actuation of the movable component.

In other aspects of the present disclosure, the movable component is manually actuated or is actuated by a powered input, e.g., from a surgical robot.

In still another aspect of the present disclosure, the motion sensor is removably attachable to the housing.

In still yet another aspect of the present disclosure, the system further includes a surgical generator connected to the surgical instrument and configured to transmit energy to the end effector assembly for treating tissue therewith. The computing device may be part of the surgical generator.

In another aspect of the present disclosure, the motion sensor includes an accelerometer.

A method of monitoring a surgical instrument in accordance with the present disclosure includes sensing a vibration signature generated from movement of a movable component of a surgical instrument relative to a housing of the surgical instrument and determining, based on the sensed vibration signature, a condition of the movable component.

In an aspect of the present disclosure, sensing the vibration signature includes sensing amplified vibrations produced by an amplification mechanism coupled to the movable component. Sensing the amplified vibrations may include at least one of sensing discrete amplified vibrations or continuous amplified vibrations.

In another aspect of the present disclosure, determining the condition of the movable component includes determining at least one of: an amount of movement of the movable component, a direction of movement of the movable component, a speed of movement of the movable component, or an acceleration of movement of the movable component.

In still another aspect of the present disclosure, the method further includes determining a condition of an end effector assembly of the surgical instrument based on the determined condition of the movable component.

In yet another aspect of the present disclosure, determining the condition of the movable component includes running at least one machine learning algorithm and/or performing comparative analysis.

In still yet another aspect of the present disclosure, the vibration signature is sensed by a motion sensor releasably attached to the surgical instrument.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

The present disclosure provides surgical instruments, systems, methods, and attachments therefor utilizing vibration feedback, e.g., to determine a position, orientation, speed, or other condition of a component or components. Various exemplary energy-based surgical instruments and systems are detailed below; however, the aspects and features of the present disclosure are not limited thereto as any other suitable surgical instruments, systems, methods, and/or attachments therefor are also contemplated for use in accordance with the present disclosure, as are non-surgical devices, systems, methods, and attachments.

Figure 1A:
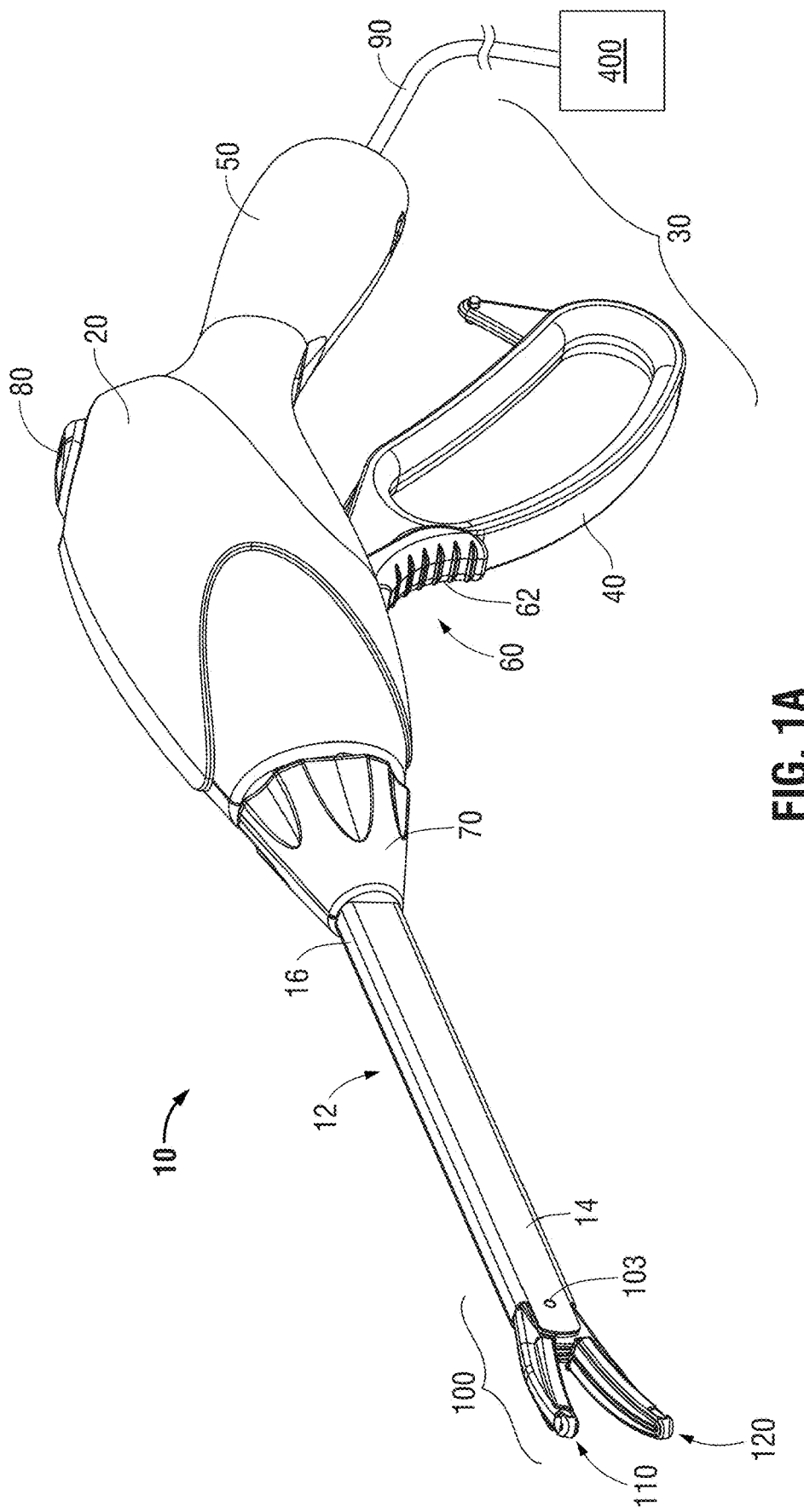
FIG. 1A is a perspective view of a shaft-based electrosurgical forceps provided in accordance with the present disclosure connected to an electrosurgical generator.

Referring to FIG. 1A, a shaft-based electrosurgical forceps provided in accordance with the present disclosure is shown generally identified by reference numeral 10. Aspects and features of forceps 10 not germane to the understanding of the present disclosure are omitted to avoid obscuring the aspects and features of the present disclosure in unnecessary detail.

Forceps 10 includes a housing 20, a handle assembly 30, a trigger assembly 60, a rotating assembly 70, an activation switch 80, and an end effector assembly 100. Forceps 10 further includes a shaft 12 having a distal end portion 14 configured to (directly or indirectly) engage end effector assembly 100 and a proximal end portion 16 that (directly or indirectly) engages housing 20. Forceps 10 also includes cable 90 that connects forceps 10 to an electrosurgical generator 400. Cable 90 includes a wire (or wires) (not shown) extending therethrough that has sufficient length to extend through shaft 12 in order to provide energy to one or both tissue-contacting surfaces 114, 124 of jaw members 110, 120, respectively, of end effector assembly 100 (see FIGS. 1B and 1C). Activation switch 80 is coupled to tissue-contacting surfaces 114, 124 (FIGS. 1B and 1C) and electrosurgical generator 400 for enabling the selective activation of the supply of energy to jaw members 110, 120 for treating, e.g., sealing, tissue.

Handle assembly 30 of forceps 10 includes a fixed handle 50 and a movable handle 40 (although both handles 40, 50 may move, in some configurations). Fixed handle 50 is integrally associated with housing 20 and handle 40 is movable relative to fixed handle 50. Movable handle 40 of handle assembly 30 is operably coupled to a drive assembly 42 (FIG. 5) that, together, mechanically cooperate to impart movement of one or both of jaw members 110, 120 of end effector assembly 100 about a pivot 103 between a spaced-apart position (FIG. 1B) and an approximated position (FIG. 1C) to grasp tissue between jaw members 110, 120. As shown in FIG. 1A, movable handle 40 is initially spaced-apart from fixed handle 50 and, correspondingly, jaw members 110, 120 of end effector assembly 100 are disposed in the spaced-apart position. Movable handle 40 is depressible from this initial position to a depressed position corresponding to the approximated position of jaw members 110, 120 (FIG. 1C).

Trigger assembly 60 includes a trigger 62 coupled to housing 20 and movable relative thereto between an un-actuated position and an actuated position. Trigger 62 is operably coupled to a knife 64 (FIG. 1B) via a trigger linkage 66 and knife bar 68 (see FIG. 5), so as to enable actuation of knife 64 (FIG. 1B) to cut tissue grasped between jaw members 110, 120 of end effector assembly 100 upon actuation of trigger 62. As an alternative to knife 64, other suitable mechanical, electrical, or electromechanical cutting mechanisms (stationary or movable) are also contemplated.

Figure 1B:
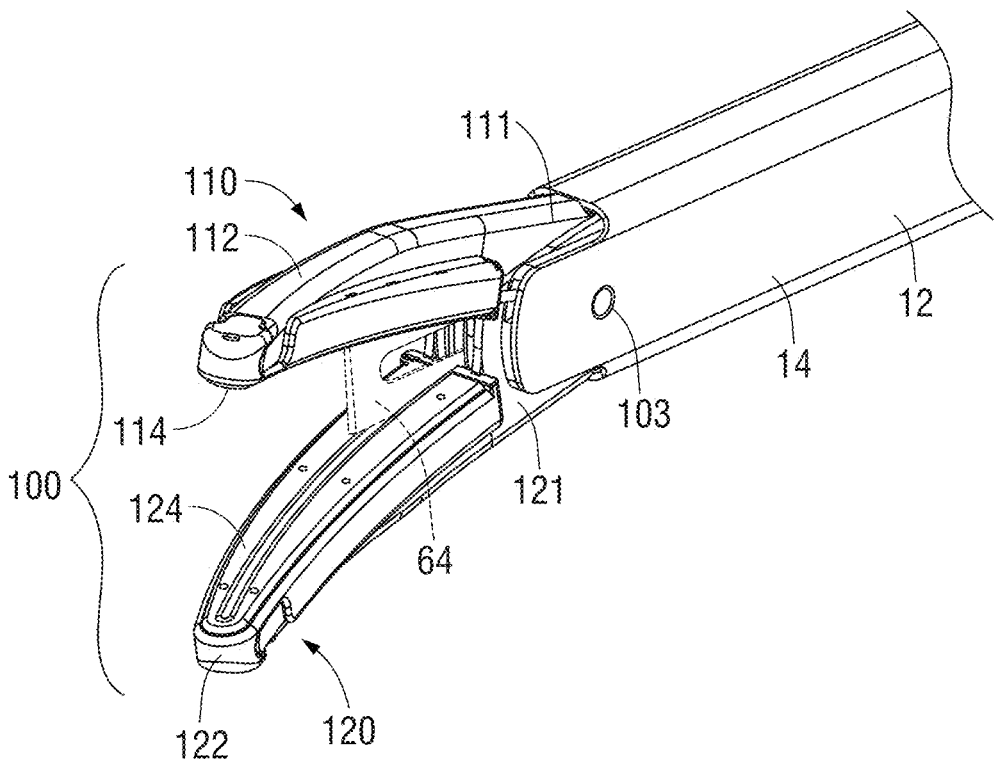
FIG. 1B is a perspective view of a distal end portion of the forceps of FIG. 1A, wherein jaw members of an end effector assembly of the forceps are disposed in a spaced-apart position.
Figure 1C:
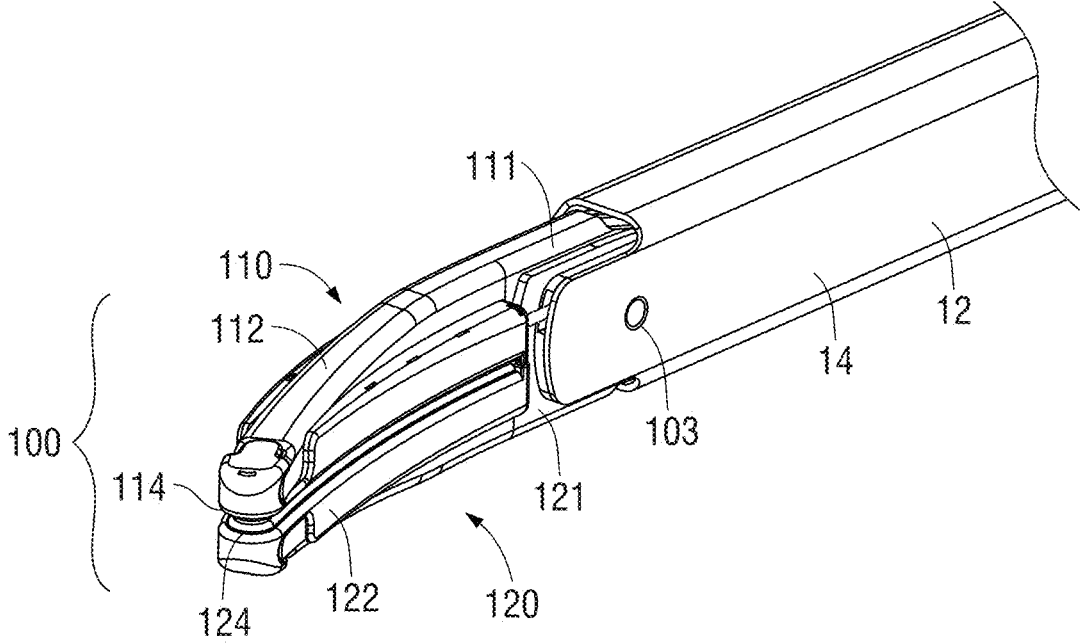
FIG. 1C is a perspective view of the distal end portion of the forceps of FIG. 1A, wherein the jaw members are disposed in an approximated position.
Figures 2A, 2B:
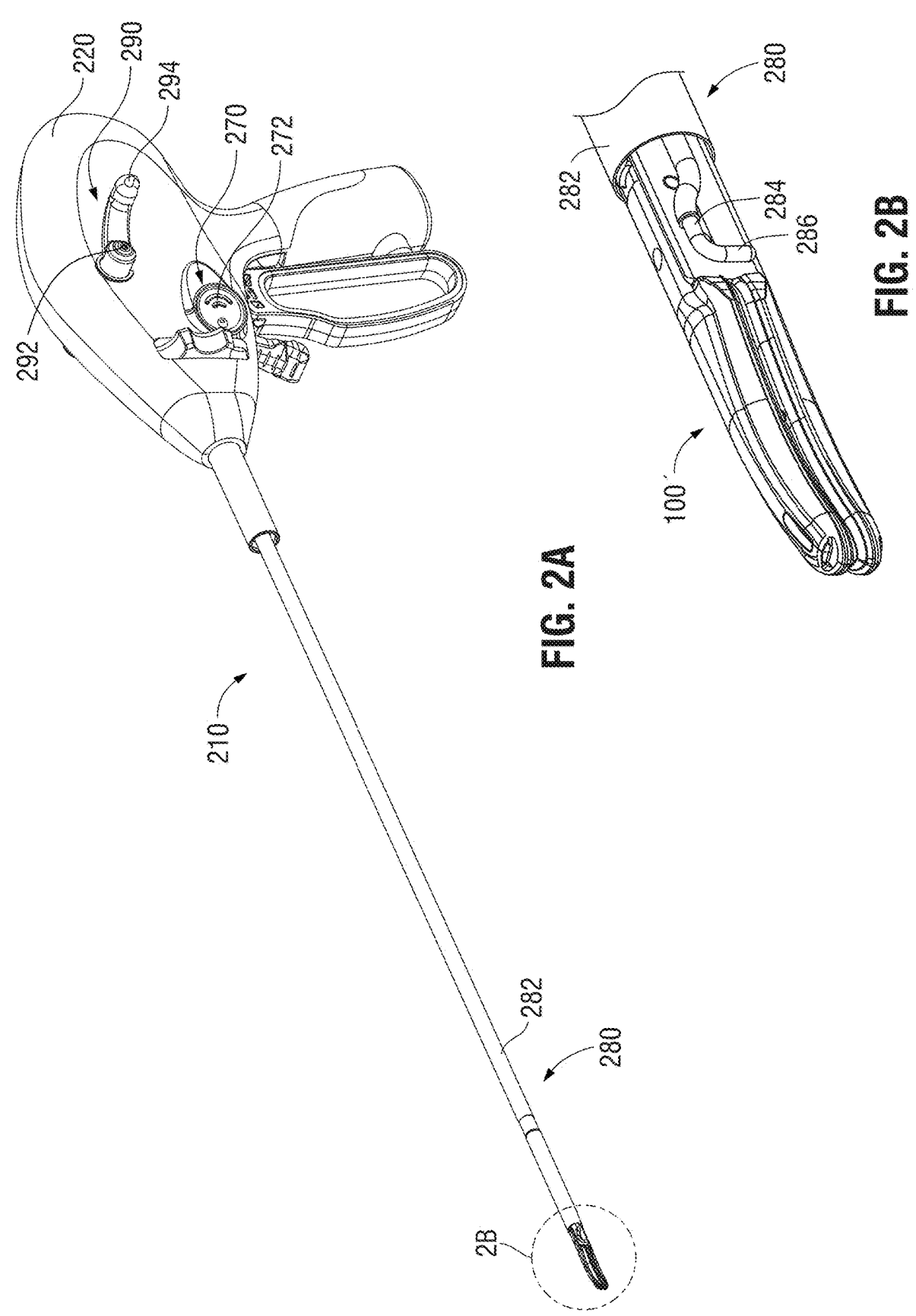
FIG. 2A is a perspective view of a shaft-based multi-function instrument provided in accordance with the present disclosure, with a deployable assembly thereof disposed in a retracted position.
FIG. 2B is an enlarged, perspective view of the area of detail indicated as "2B" in FIG. 2A.
Figure 2C:
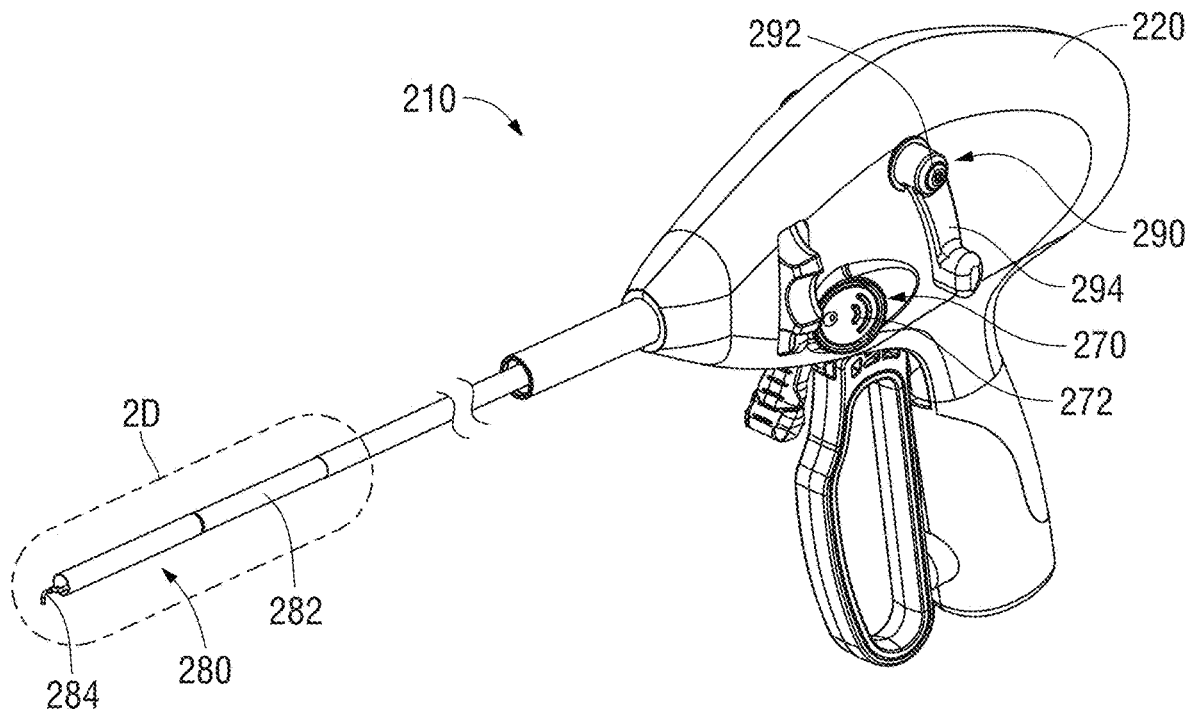
FIG. 2C is a perspective view of the shaft-based multi-function instrument of FIG. 2A with the deployable assembly thereof disposed in an extended position.
Figure 2D:
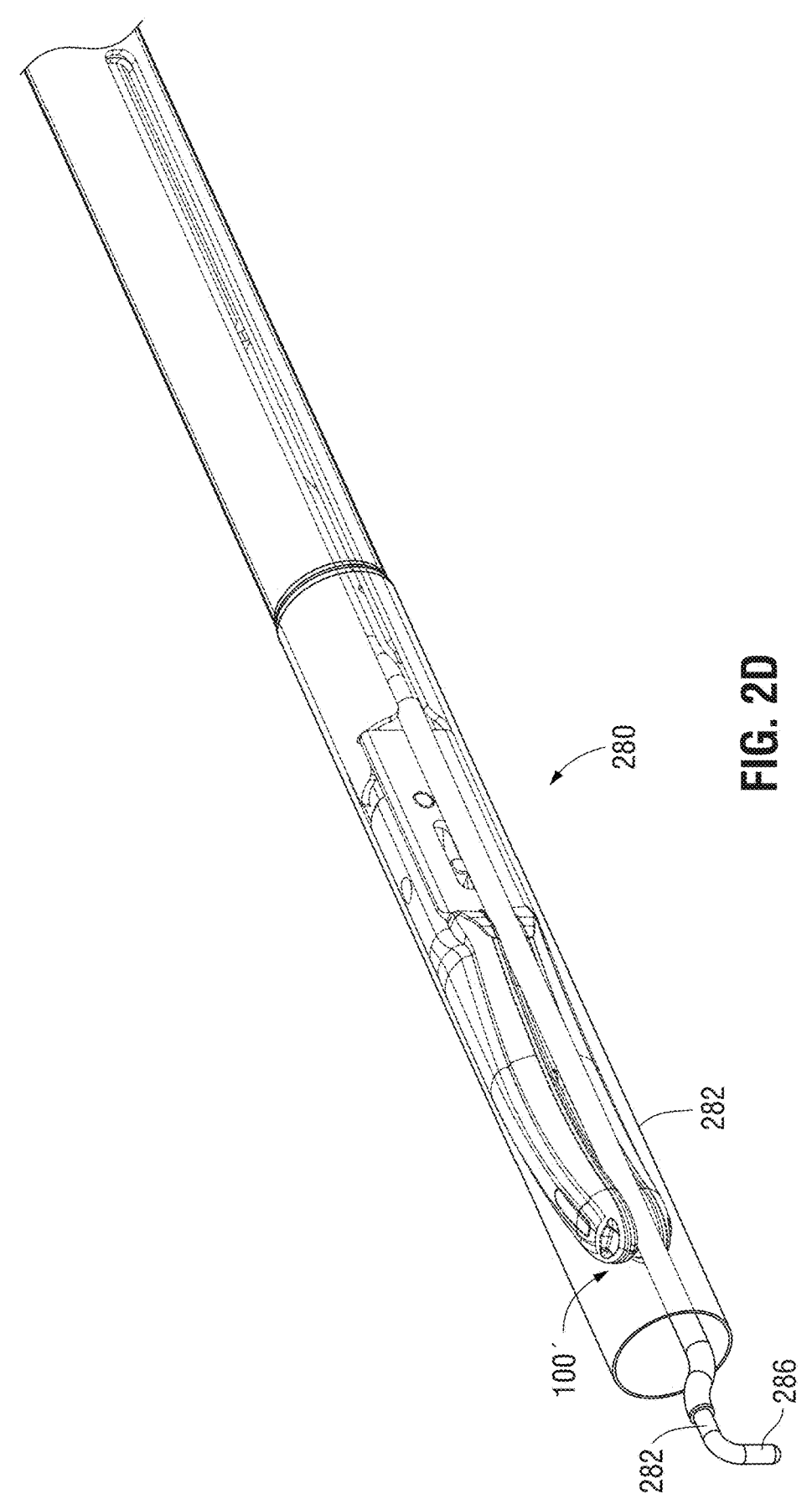
FIG. 2D is an enlarged, perspective view of the area of detail indicated as "2D" in FIG. 2C.

With additional reference to FIGS. 1B and 1C, end effector assembly 100, as noted above, includes first and second jaw members 110, 120. Each jaw member 110, 120 includes a proximal flange portion 111, 121, an outer insulative jaw housing 112, 122 disposed about the distal portion (not explicitly shown) of each jaw member 110, 120, and a tissue-contacting surface 114, 124, respectively. Proximal flange portions 111, 121 are pivotably coupled to one another about pivot 103 for moving jaw members 110, 120 between the spaced-apart and approximated positions, although other suitable mechanisms for pivoting jaw members 110, 120 relative to one another are also contemplated. The distal portions (not explicitly shown) of the jaw members 110, 120 are configured to support jaw housings 112, 122, and tissue-contacting surfaces 114, 124, respectively, thereon.

Outer insulative jaw housings 112, 122 of jaw members 110, 120 support and retain tissue-contacting surfaces 114, 124 on respective jaw members 110, 120 in opposed relation relative to one another. Tissue-contacting surfaces 114, 124 are at least partially formed from an electrically conductive material, e.g., for conducting electrical energy therebetween for treating tissue, although tissue-contacting surfaces 114, 124 may alternatively be configured to conduct any suitable energy, e.g., thermal, microwave, light, ultrasonic, etc., through tissue grasped therebetween for energy-based tissue treatment. As mentioned above, tissue-contacting surfaces 114, 124 are coupled to activation switch 80 and electrosurgical generator 400, e.g., via the wires (not shown) extending from cable 90 through forceps 10, such that energy may be selectively supplied to tissue-contacting surface 114 and/or tissue-contacting surface 124 and conducted therebetween and through tissue disposed between jaw members 110, 120 to treat tissue.

With reference to FIGS. 2A-2D, a multi-function surgical instrument provided in accordance with the present disclosure is shown generally identified by reference numeral 210. Instrument 210 includes similar features as forceps 10 (FIGS. 1A-1C) except that instrument 210 further includes a second activation assembly 270, a deployable assembly 280, and a deployment and retraction mechanism 290 and, thus, only these additional features are detailed below.

Deployable assembly 280 includes a sheath 282 and an energizable member 284. Sheath 282, in embodiments, is insulative, although other configurations are also contemplated. Sheath 282 is movable relative to end effector assembly 100' between a retracted position, wherein sheath 282 is disposed proximally of end effector assembly 100', and an extended position, wherein sheath 282 is substantially disposed about end effector assembly 100'. Energizable member 284 is coupled to generator 400 (FIG. 1A) and second activation assembly 270 via one or more wires (not shown) and may function as the active electrode of a monopolar circuit or may be energizable with any other suitable form of energy, e.g., thermal, microwave, etc. Energizable member 284 is movable together with sheath 282 and relative to end effector assembly 100' between a retracted position, wherein distal tissue-treating portion 286 of energizable member 284 is positioned more-proximally, and an extended position, wherein distal tissue-treating portion 286 of energizable member 284 extends distally from end effector assembly 100' to facilitate treating tissue therewith. Energizable member 284, more specifically, is engaged with sleeve 282 such that energizable member 284 and sleeve 282 move together between their respective retracted and extended positions (collectively the retracted and extended positions of deployable assembly 280). In the extended position, in embodiments where sheath 282 is insulative, sheath 282 serves to electrically insulate end effector assembly 100' from distal tissue-treating portion 286 of energizable member 284, while distal tissue-treating portion 286 extends distally from end effector assembly 100'. In the extended position, energy may be supplied to distal tissue-treating portion 286 of energizable member 284, e.g., via activation of either of the activation switches 272 of second activation assembly 270, for treating, e.g., dissecting, tissue.

Deployment and retraction mechanism 290 is configured for selectively transitioning deployable assembly 280 between its retracted position and its extended position. Deployment and retraction mechanism 290 generally includes a gear assembly (not shown) disposed within housing 220, a pair of input shafts 292 operably coupled to the gear assembly and extending transversely from either side of housing 220, a pair of deployment paddles 294 operably coupled to the input shafts 292 (only one side of housing 220 and, thus, one paddle 294 is illustrated), and a slider (not shown) disposed within housing 220 and operably coupling an output of the gear assembly with energizable member 284 of deployable assembly 280 (which, in turn, is engaged with sheath 282) such that deployment and retraction mechanism 290 is configured to enable both deployment and retraction of deployable assembly 280 in a push-push manner, e.g., wherein deployable assembly 280 is both deployed and retracted by pushing either of paddles 294 in the same direction. Other configurations are also contemplated. Further, as opposed to a multi-function instrument, an instrument including just an energizable member 284 of any suitable configuration and/or energy (monopolar, bipolar, thermal, etc.) is also contemplated.

Figure 3:
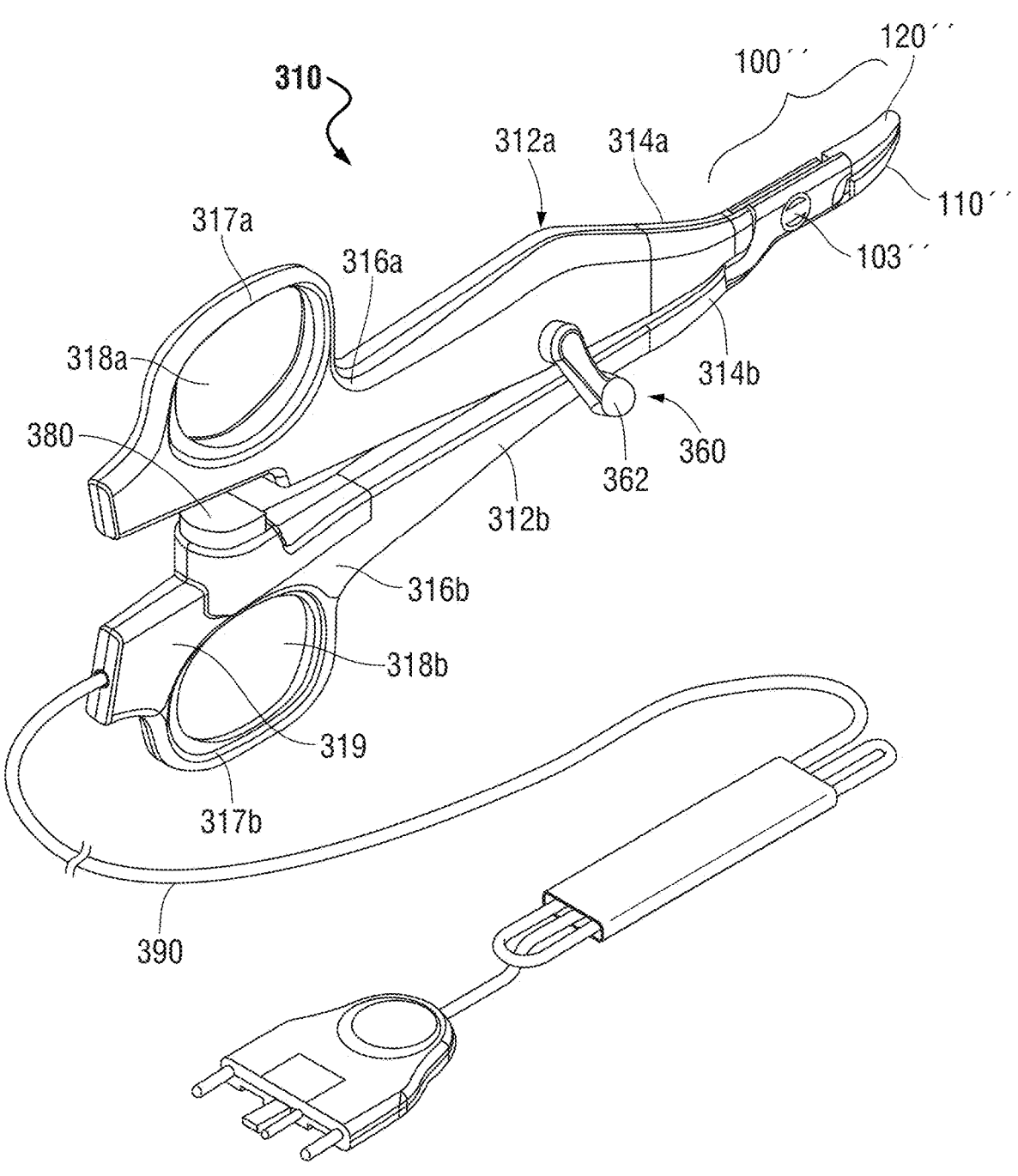
FIG. 3 is a perspective view of a hemostat-style electrosurgical forceps provided in accordance with the present disclosure.

Referring to FIG. 3, a hemostat-style electrosurgical forceps provided in accordance with the present disclosure is shown generally identified by reference numeral 310. Aspects and features of forceps 310 not germane to the understanding of the present disclosure are omitted to avoid obscuring the aspects and features of the present disclosure in unnecessary detail.

Forceps 310 includes two elongated shaft members 312a, 312b, each having a proximal end portion 316a, 316b, and a distal end portion 314a, 314b, respectively. Forceps 310 is configured for use with an end effector assembly 100" similar to end effector assembly 100 (FIGS. 1B and 1C). More specifically, end effector assembly 100" includes first and second jaw members 110", 120" attached to respective distal end portions 314a, 314b of shaft members 312a, 312b. Jaw members 110", 120" are pivotably connected about a pivot 103". Each shaft member 312a, 312b includes a handle 317a, 317b disposed at the proximal end portion 316a, 316b thereof. Each handle 317a, 317b defines a finger hole 318a, 318b therethrough for receiving a finger of the user. As can be appreciated, finger holes 318a, 318b facilitate movement of the shaft members 312a, 312b relative to one another to, in turn, pivot jaw members 110", 120" from the spaced-apart position, wherein jaw members 110", 120" are disposed in spaced relation relative to one another, to the approximated position, wherein jaw members 110", 120" cooperate to grasp tissue therebetween.

One of the shaft members 312a, 312b of forceps 310, e.g., shaft member 312b, includes a proximal shaft connector 319 configured to connect forceps 310 to electrosurgical generator 400 (FIG. 1A). Proximal shaft connector 319 secures a cable 390 to forceps 310 such that the user may selectively supply energy to jaw members 110", 120" for treating tissue. More specifically, an activation switch 380 is provided for supplying energy to jaw members 110", 120" to treat tissue upon sufficient approximation of shaft members 312a, 312b, e.g., upon activation of activation switch 380 via shaft member 312a.

Forceps 310 further includes a trigger assembly 360 including a trigger 362 coupled to one of the shaft members, e.g., shaft member 312a, and movable relative thereto between an un-actuated position and an actuated position. A portion of shaft member 312a serves as a housing that houses a knife assembly (not shown) operably coupled to trigger 362. Trigger 362, more specifically, is operably coupled to a knife (not shown; similar to knife 64 (FIG. 1B) of forceps 10 (FIG. 1A)) of the knife assembly so as to actuate the knife to cut tissue grasped between jaw members 110", 120" of end effector assembly 100" upon movement of trigger 362 to the actuated position. Similarly as noted above with respect to forceps 10 (FIG. 1A), other suitable cutting mechanisms are also contemplated.

Figure 4:
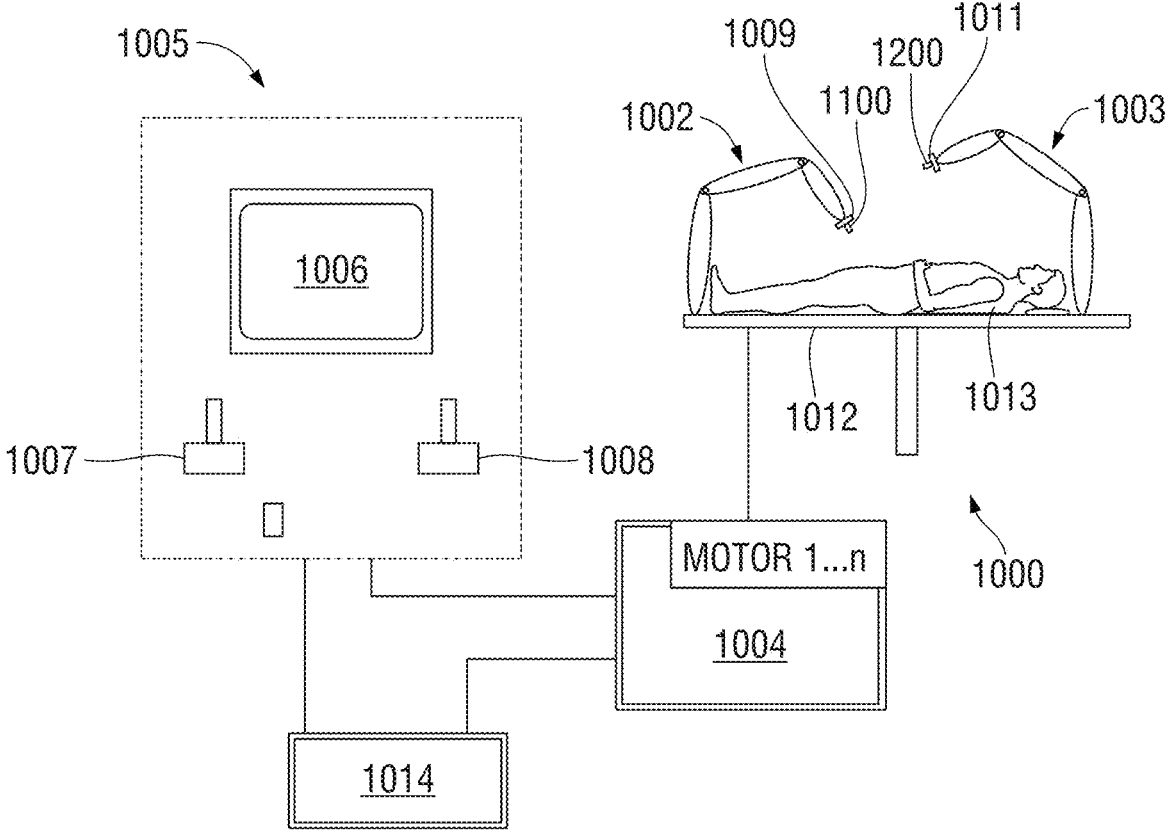
FIG. 4 is a schematic illustration of a robotic surgical instrument provided in accordance with the present disclosure.

Referring to FIG. 4, a robotic surgical instrument provided in accordance with the present disclosure is shown generally identified by reference numeral 1000. Aspects and features of robotic surgical instrument 1000 not germane to the understanding of the present disclosure are omitted to avoid obscuring the aspects and features of the present disclosure in unnecessary detail.

Robotic surgical instrument 1000 includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by which a surgeon may be able to telemanipulate robot arms 1002, 1003 in a first operating mode. Robotic surgical instrument 1000 may be configured for use on a patient 1013 lying on a patient table 1012 to be treated in a minimally invasive manner. Robotic surgical instrument 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, an end effector assembly 1100, 1200, respectively. End effector assembly 1100 is similar to end effector assembly 100 (FIGS. 1B and 1C), although other suitable end effector assemblies for coupling to attaching device 1009 are also contemplated. End effector assembly 1100 is connected to electrosurgical generator 400 (FIG. 1A), which may be integrated into or separate from robotic surgical instrument 1000. End effector assembly 1200 may be any end effector assembly, e.g., an endoscopic camera, other surgical tool, etc. Robot arms 1002, 1003 and end effector assemblies 1100, 1200 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and end effector assemblies 1100, 1200 execute a desired movement and/or function according to a corresponding input from manual input devices 1007, 1008, respectively. Control device 1004 may also be configured in such a way that it regulates the movement of robot arms 1002, 1003 and/or of the motors.

Figure 5:
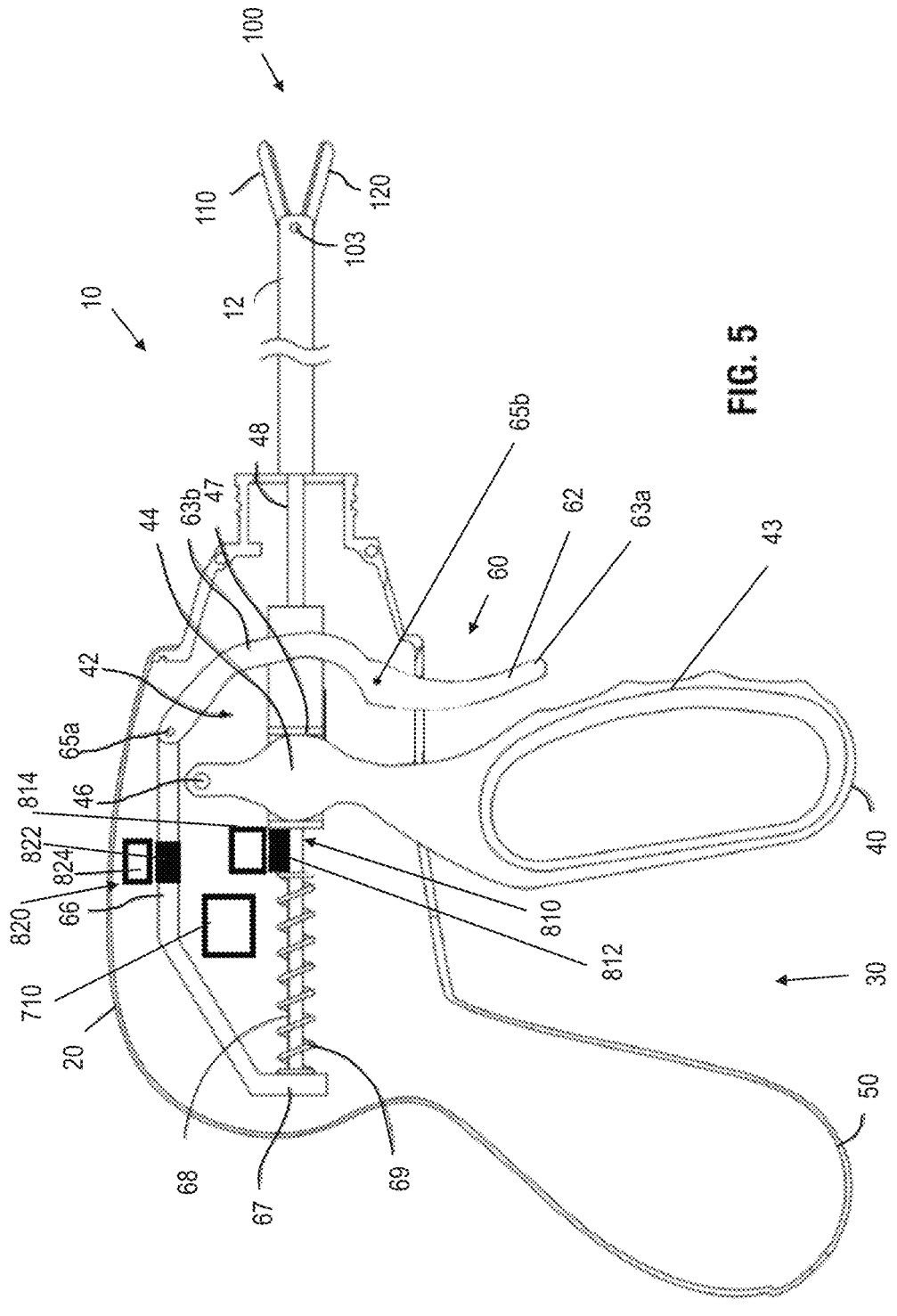
FIG. 5 is a side, partial longitudinal, cross-sectional view of the forceps of FIG. 1A.

Turning to FIG. 5, as noted above, forceps 10, includes movable handle 40 operably coupled to drive assembly 42 to impart movement of one or both of jaw members 110, 120 of end effector assembly 100 about a pivot 103 between the spaced-apart position (FIG. 1B) and the approximated position (FIG. 1C). Movable handle 40, more specifically, includes a lever portion 43 extending from housing 20 to enable manual manipulation thereof by a user and a drive portion 44 extending upwardly from lever portion 43 into housing 20. Drive portion 44 is bifurcated into first and second spaced-apart flanges 45 that are pivotably coupled to housing 20 towards the free ends thereof via a pivot pin 46. Flanges 45 extend on either side of drive assembly 42 and are coupled thereto to facilitate movement of jaw members 110, 120 between the spaced-apart position and the approximated position. More specifically, flanges 45 extend upwardly on either side of mandrel 47 of drive assembly 42 and are disposed within lateral slots defined by mandrel 47 such that pivoting of lever portion 43 of movable handle 40 about pivot pin 46 and relative to housing 20 translates mandrel 47 longitudinally relative to housing 20. Mandrel 47, in turn, is operably coupled to drive bar 48 of drive assembly 42 (e.g., fixedly, via a spring assembly, or in any other suitable manner) such that translation of mandrel 47 translates drive bar 48. Drive bar 48 extends from housing 20 and through shaft 12 to end effector assembly 100 wherein drive bar 48 is operably coupled to either or both jaw members 110, 120 (e.g., via a cam-slot mechanism or in any other suitable manner) such that translation of drive bar through shaft 12 and relative to end effector assembly pivot jaw member(s) 110, 120 between the spaced-apart (FIG. 1B) and approximated (FIG. 1C) positions.

As also noted above, trigger assembly 60 includes trigger 62 operably coupled to a knife 64 (FIG. 1B) via a trigger linkage 66 and knife bar 68 (see FIG. 5), to enable actuation of knife 64 (FIG. 1B) to cut tissue grasped between jaw members 110, 120 of end effector assembly 100 upon actuation of trigger 62. Trigger 62, more specifically, includes a toggle portion 63*a* extending from housing 20 to enable manual manipulation thereof by a user and an arm portion 63*b* extending upwardly from toggle portion 63*a* and into housing 20. Arm portion 63*b* is pivotably coupled, at an intermediate portion thereof, to housing 20 via a pivot pin 65*a*, and, at a free end portion thereof, to trigger linkage 66 via a pivot pin 65*b*. Trigger linkage 66, in turn, defines a pusher end portion 67 operably coupled with knife bar 68. In this manner, upon pivoting of toggle portion 63*a* of trigger 62 about pivot pin 65*a* and relative to housing 20, trigger linkage 66 is moved through housing 20 to, in turn, translate knife bar 68 through and relative to housing 20. In aspects, knife bar 68 is slidably disposed within drive bar 48 (as shown), although the opposite configuration is also contemplated as are configurations wherein drive bar 48 and knife bar 68 extend through shaft 12 in substantially parallel but offset relation relative to one another. Kinfe bar 68 supports knife 64 (FIG. 1B) at the distal end thereof and, thus, upon translation of knife bar 68 in response to actuation of trigger 62, knife 64 (FIG. 1B) is translated relative to end effector assembly 100 between the retracted and extends positions. In aspects, a return spring 69 biases knife 64 (FIG. 1B) towards the retracted position and trigger 62 towards the un-actuated position and/or biases movable handle 40 towards the initial position and jaw members 110, 120 towards the spaced-apart position.

Continuing with reference to FIG. 5, as detailed above, various components are pivoted, rotated, and/or translated to enable pivoting of jaw members 110, 120 and deployment of knife 64 (FIG. 1). Likewise, in order to operate surgical instrument 210 (FIGS. 2A-2D), surgical instrument 310 (FIG. 3), surgical instrument 1000 (FIG. 4), as well as any other suitable surgical instruments, mechanical movement, e.g., pivoting, rotation, and/or translation, of one or more components is required. Each of these motions produces vibrations in the moving component(s) and/or surrounding components. Detection of vibrations, e.g., using a motion sensor 710 and, in aspects, an amplification mechanism(s) 810, 820, associated with these motions can thus be utilized to determine a vibration signature, e.g., providing direction, magnitude, speed, acceleration, and/or other information about the moving component(s), which, in turn, can be utilized to determine a position, orientation, status, speed, acceleration, state, and/or other condition of the surgical instrument, sub-assembly(s) thereof, and/or component(s) thereof. Although detailed below with respect to determining jaw position via a vibration signature associated with movement of drive bar 48 and knife position via a vibration signature associated with trigger linkage 66, the present disclosure may apply equally to detecting vibration of any suitable moving component(s), moving in any suitable manner, in order to determine information about the component or a condition resulting from movement of that component based on a detected vibration signature. In aspects, the vibration signature may also inform regarding a size, type, and/or property of tissue that the surgical instrument, e.g., jaw members 110, 120 thereof, is interacting with. Further, it is noted that the movement and resulting condition need not be related to deployment or actuation of a component or components but, rather, may relate to other aspects of operation of a surgical (or other) instrument such as, for example, rotation, articulation, etc.

In order to enable the above-detailed vibration sensing, a motion sensor 710 is employed. Motion sensor 710 may be a 3-axis motion sensor (e.g., a 3-axis accelerometer, a 3-axis gyroscope, a 3-axis magnetometer, or other suitable 3-axis motion sensor or combination of motion sensors to provide 3-axis motion sensing); a 6-axis motion sensor (e.g., any two of the above or other suitable motion sensor(s) or combinations thereof); a 9-axis motion sensor (e.g., any three of the above or other suitable motion sensor(s) or combinations thereof); or any other suitable motion sensor configured to sense vibrations. Motion sensor 710 may be disposed on or within housing 20, or otherwise positioned on or within a portion of forceps 10 to enable motion sensor 710 to sense vibrations, e.g., in response to movement of drive bar 48 and/or trigger linkage 66. In configurations where motion sensor 710 is disposed within housing 20 or otherwise integrated on or within forceps 10, motion sensor 710 may be electrically coupled to generator 400 (FIG. 1A), e.g., via one or more wires extending through housing 20 and cable 90 (FIG. 1A) or wirelessly. In configurations wherein motion sensor 710 is removably attached to housing 20 or another portion of forceps 10, motion sensor 710 may include one or more wires for coupling motion sensor 710 to generator 400 (FIG. 1A) independently of the coupling of forceps 10 thereto, or may incorporate a wireless transceiver to enable wireless communication with generator 400 (FIG. 1A), e.g., via WiFi, Bluetooth, IR communication, etc. As an alternative to connecting to generator 400 (FIG. 1A), motion sensor 710 may be configured to connect, e.g., via a wired or wireless connection, to any other suitable computing device, e.g., an operating room tower, display, tablet, smartphone, smartwatch, smart glasses, laptop computer, desktop computer, one or more networked (physical or virtual) servers, etc. Motion sensor 710 may be removably attached to forceps 10 using a mechanical engagement, e.g., clip, latch, etc., adhesive, or in any other suitable manner. Removable attachment of motion sensor 710 (and the independent connection thereof) enables motion sensor 710 to be retrofitted to any suitable device and/or utilized in a variety of different devices, whether surgical instruments or other devices and for a variety of purposes, e.g., to provide condition information during use, for confirmatory testing after manufacture, for evaluation testing after use and/or reprocessing, etc. In aspects where motion sensor 710 is removably attachable to forceps 10 and/or other surgical instruments, motion sensor 710 may thus form an attachment for use with forceps 10 and/or other surgical instruments. The attachment may include motion sensor 710, a housing enclosing motion sensor 710 and configured to releasably attach to forceps 10 and/or other surgical instruments, and communication device, e.g., a cable and plug including connecting wires, or a wireless transceiver. In aspects, the attachment may further include a power source, e.g., a battery, to power the attachment.

Referring still to FIG. 5, in order to enhance the ability of motion sensor 710 to sense vibrations associated with movement of drive bar 48 and/or trigger linkage 66, and/or to facilitate identification of a vibration signature thereof, one or more amplification mechanisms 810, 820 may be provided, although in other aspects, amplification mechanisms 810, 820 may be omitted (for example, depending upon the movement and/or condition to be determined, a level of vibration produced, other vibration noise, a sensitivity of the motion sensor, etc.). Amplification mechanisms 810, 820 more specifically, are configured to produce an amplified vibration in response to movement of drive bar 48 and/or trigger linkage 66 (as compared to movement of drive bar 48 and/or trigger linkage 66 without amplification; the amplification mechanisms need not amplify pre-existing vibrations or produce vibrations similar to pre-existing vibrations), thus facilitating detection of the vibration via motion sensor 710 and/or the processing thereof, as detailed below. In aspects, first amplification mechanism 810 includes a first component 812 coupled to drive bar 48 and configured to move therewith and a second component 814 coupled to housing 20 such that, upon movement of drive bar 48 relative to housing 20, first component 812 interacts with second component 814 to produce vibrations. Likewise, second amplification mechanism 820 may include a first component 822 coupled to trigger linkage 66 and configured to move therewith and a second component 824 coupled to housing 20 such that, upon movement of trigger linkage 66 relative to housing 20, first component 822 interacts with second component 824 to produce vibrations. In aspects, motion sensor 710 is disposed on second component 814 or second component 814. In aspects, multiple motion sensors 710 are provided, e.g., one for each amplification mechanism 810, 820 (or movable component, where amplification mechanisms 810, 820 are omitted).

Figures 6A, 6B, 6C:
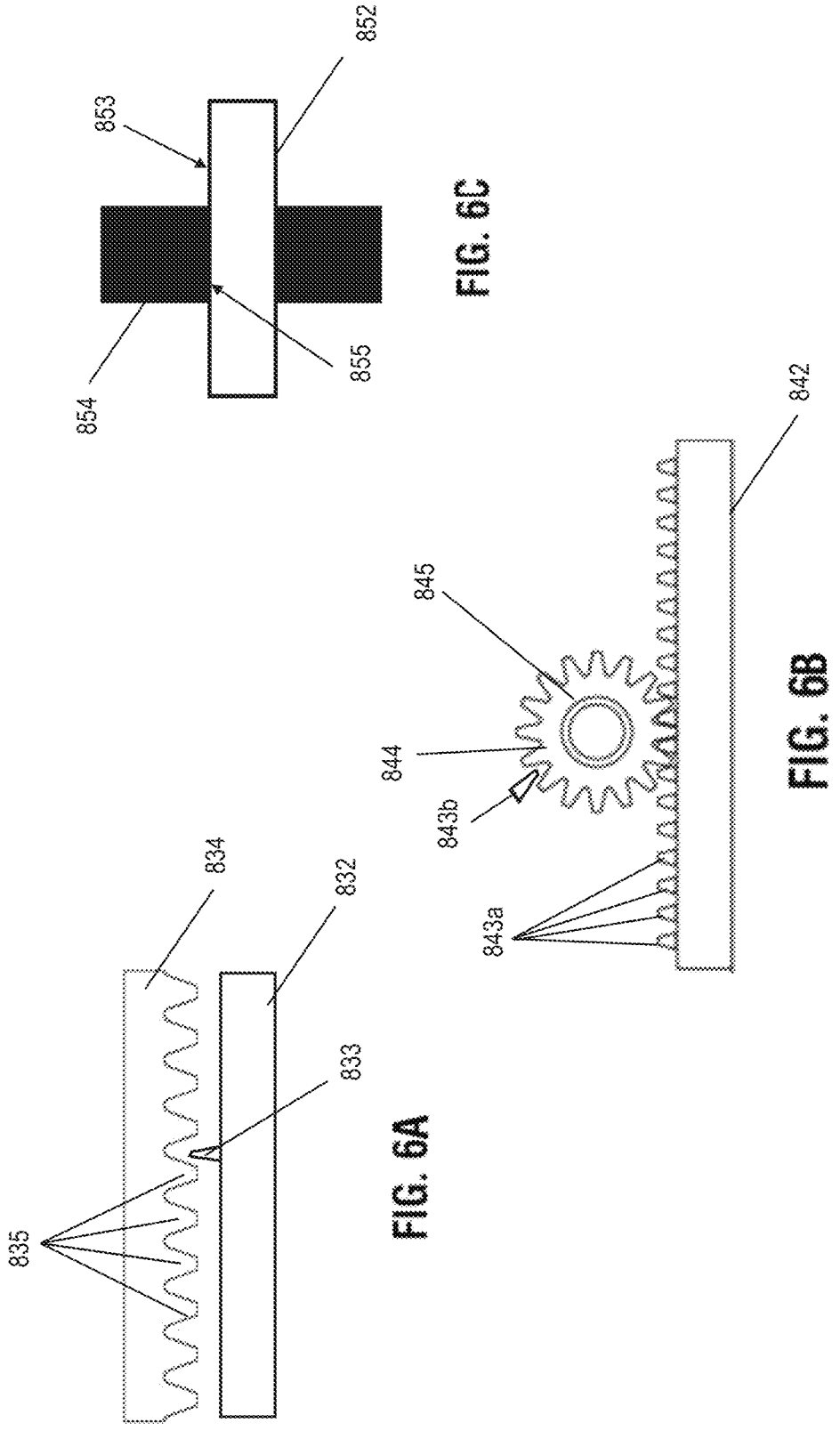
FIGS. 6A-6C are side views of various vibration amplification mechanisms in accordance with the present disclosure.

FIGS. 6A-6C illustrate exemplary first and second components 832, 842, 852 and 834, 844, 854, respectively, configured for use as first and second components 812, 822 and 814, 824 of first and/or second amplification mechanisms 810, 820, respectively (see FIG. 5), although other suitable interacting component configurations are also contemplated. With particular reference to FIG. 6A, first component 832 includes a pick 833 while second component 834 includes a plurality of spaced-apart teeth 835 along a portion of a length thereof, although this configuration may be reversed or both components 832, 834 may include a plurality of teeth 835. Upon relative movement, e.g., translation, between first and second components 832, 834, respectively, pick 833 is translated along and interacts with, e.g., contacts and deflects and/or is deflected by, teeth 835, thereby producing vibrations. In aspects, teeth 835 may be the same or different height, thickness, flexibility, materials, shape profile, etc., and/or may be spaced equal or different distances to vary the vibrations produced as pick 833 interacts with different teeth 835, thus facilitating distinguishing a particular vibration signature. As an alternative to pick 833 translating relative to teeth 835, pick 833 may be stationary while teeth 835 are translated relative thereto. That is, components 832 and 834 may be reversed.

With particular reference to FIG. 6B, first component 842 is configured as a rack including at least one pick, e.g., a plurality of spaced-apart picks 843a along a portion of a length thereof, while second component 844 includes a pinion gear 845. Upon relative movement between first and second components 842, 844, respectively, picks 843a interact with, e.g., contact and urge rotation of, the teeth of pinion gear 845, thereby rotating pinion gear 845. The rotation of pinion gear 845 and/or the interaction between picks 843a and pinion gear 845 produces vibrations. In aspects, picks 843a may be the same or different height, thickness, flexibility, materials, shape profile, etc., and/or may be spaced equal or different distances to vary the vibrations produced, thus facilitating distinguishing a particular vibration signature. In aspects, pinion gear 845 may be configured as a compound gear having two or more gears (of similar or different size) with gear teeth (of similar or different configuration). In such aspects, plural first components 842 may be provided, e.g., adjacent one another, wherein each first component 842 includes one or more picks configured to interact with one of the gears of the compound pinion gear 845. In aspects, rather than the teeth of first component 842 being configured as picks configured to produce the vibrations in response to interaction with pinion gear 845, one or more separate picks 843b may be provided. Pick(s) 843b may be configured similar to, function similar to, and/or include any of the features of picks 843a detailed above except that picks 843b are separate from first component 842.

With particular reference to FIG. 6C, first component 852 may be a portion of or a feature disposed on drive bar 48 and/or trigger linkage 66 (see FIG. 5) and defines an outer surface 853. Second component 854 contacts and, in aspects, at least partially surrounds first component 852. Second component 854 defines an inner surface 855 at least partially contacting outer surface 853. Upon relative movement between first and second components 852, 854, respectively, outer and inner surfaces 853, 855, respectively, interact with, e.g., frictionally slide relative to, one another to produce vibrations. In aspects, outer surface 853 and/or inner surface 855 includes a roughened and/or textured surface that may be uniform, or that is variable along a length to vary the vibrations produced, thus facilitating distinguishing a particular vibration signature. The textured surfaces of outer surface 853 and/or inner surface 855 may be similar or different, or only one of surfaces 853, 855 may include texture.

Figure 7:
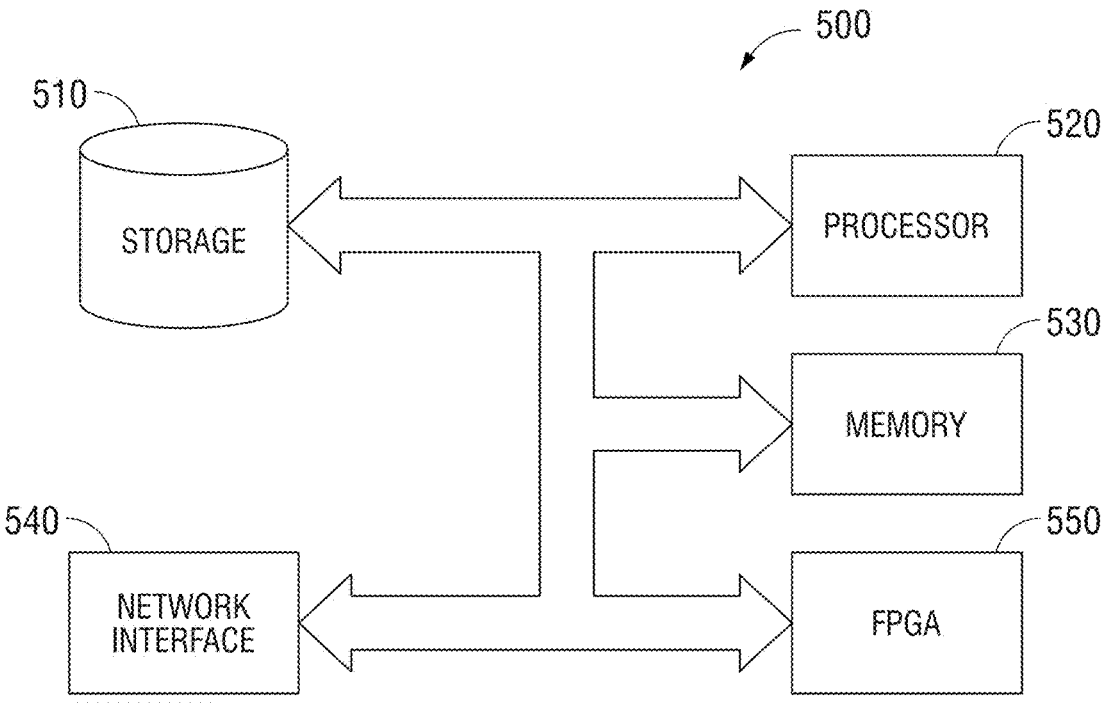
FIG. 7 is a block diagram of a controller in accordance with the present disclosure.

Turning to FIG. 7, in conjunction with FIG. 5, a controller 500 of generator 400 (FIG. 1A) or other suitable computing device configured to communicate with motion sensor 710 to receive sensed vibration data therefrom is shown as a schematic block diagram. Controller 500, more specifically, is configured to receive the sensed vibration data from motion sensor 710 and, based thereon, determine a vibration signature, e.g., a magnitude, frequency, and/or direction of vibrations over time, from which movement of drive bar 48 and/or trigger linkage 66 can be determined. Controller 500 may further be configured, based on the determined movement of drive bar 48 and/or linkage 66, to determine a position of jaw members 110, 120 (e.g., the spaced-apart position, the approximated position, or any position therebetween) and/or knife 64 (FIG. 1B, e.g., the retracted position, the extended position, or any position therebetween). This determination may be made based upon kinematics of the system, e.g., the position of jaw members 110, 120 and/or knife 64 (FIG. 1B) based on movement of the respective drive components thereof. Controller 500 may perform the above determinations in real-time (allowing computer processing time within a suitable real-time constraint), e.g., for use during a surgical procedure, or in any other suitable manner, e.g., the vibration data may be saved and later processed for training purposes, performance evaluation, device testing, etc. Controller 500 may perform these determinations, for example, via comparative analysis by comparing a detected vibration signature to a database of known vibration signatures to determine a match, via a fixed algorithm determining movement of drive bar 48 and/or linkage 66 (and, in aspects, the position of jaw members 110, 120 and/or knife 64 (FIG. 1B)) based on a detected vibration signature, utilizing one or more machine learning algorithms, or in any other suitable manner.

Controller 500 includes a processor 520 connected to a computer-readable storage medium or a memory 530 which may be a volatile type memory, e.g., RAM, or a non-volatile type memory, e.g., flash media, disk media, etc. Processor 520 may be, without limitation, a digital signal processor, a microprocessor, an ASIC, a graphics processing unit (GPU), field-programmable gate array (FPGA), or a central processing unit (CPU). Memory 530 can be random access memory, read-only memory, magnetic disk memory, solid state memory, optical disc memory, and/or another type of memory. Memory 530 can be separate from controller 500 and can communicate with processor 520 through communication buses of a circuit board and/or through communication cables such as serial ATA cables or other types of cables. Memory 530 includes computer-readable instructions that are executable by processor 520 to operate controller 500. In aspects, controller 500 includes a network interface 540 or other suitable input/output device to communicate with motion sensor 710 and/or other computing devices. In aspects, a storage device 510 may be used for storing data. Controller 500 may further include one or more FPGAs 550 for executing various algorithms, e.g., fixed algorithms, machine learning algorithms, etc.

Memory 530 stores suitable instructions, to be executed by processor 520, for receiving the sensed data, e.g., sensed vibration data from motion sensor 710, accessing storage device 510 of controller 500, and determining, from a vibration signature of the sensed vibration data, the corresponding movement to determine the position of jaw members 110, 120 and/or knife 64 (FIG. 1). Memory 530 further stores suitable instructions, to be executed by processor 520, to provide feedback based upon the determined positions(s), e.g., outputting a visual display of the position, outputting an alert signifying the position, etc.

Figure 8:
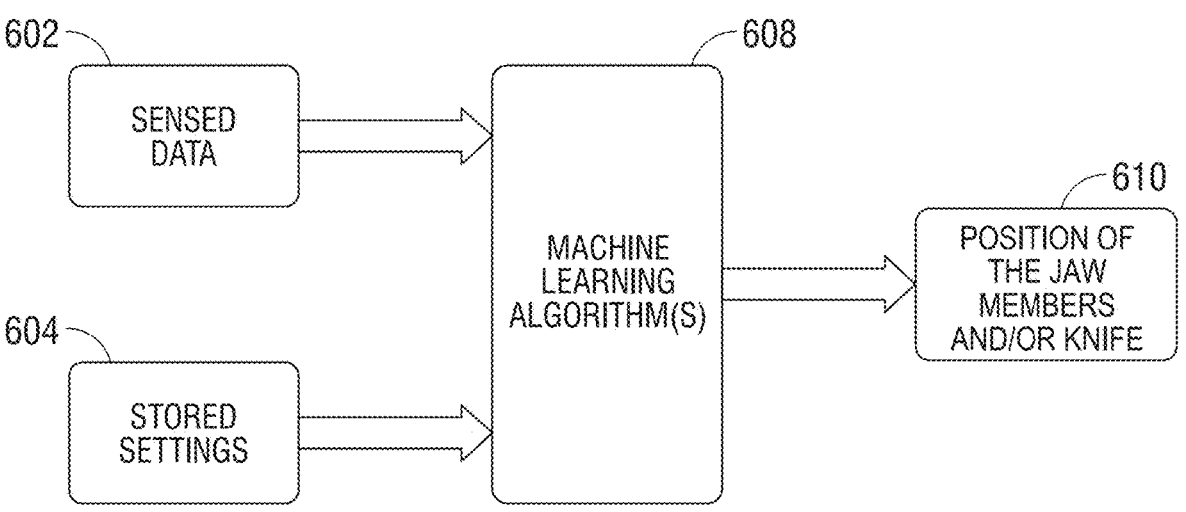
FIG. 8 is a logic diagram of a machine learning algorithm configured for use in in accordance with some aspects of the present disclosure.

With additional reference to FIG. 8, in configurations where one or more machine learning algorithms 608 are used, storage device 510 of controller 500 stores the one or more machine learning algorithms 608. The machine learning algorithm(s) 608 may be trained on and learn from stored settings 604, e.g., input experimental data and/or empirical data, in order to enable the machine learning algorithm(s) 608 to determine the output 610, e.g., the position of jaw members 110, 120 and/or knife 64 (FIG. 1i), based on the input sensed data 602, e.g., the vibration data from motion sensor 710 that provides the vibration signature. Training the machine learning algorithm(s) 608 may, in aspects, be performed by a computing device separate from controller 500 and the resulting algorithm may be communicated to controller 500.

In aspects, the one or more machine learning algorithms 608 may include classification machine learning and/or one or more neural networks such as, for example, a long-short term memory network, a convolutional neural network (CNN), a recurrent adversarial network (RAN), a generative adversarial network (GAN) and/or other suitable neural network(s). As an alternative or in addition to a neural network, other suitable machine learning systems may be utilized such as, for example a support vector machine (SVM), and/or may implement: Bayesian Regression, Naive Bayes, nearest neighbors, least squares, means, and support vector regression, among other data science and artificial science techniques.

Figure 9A:
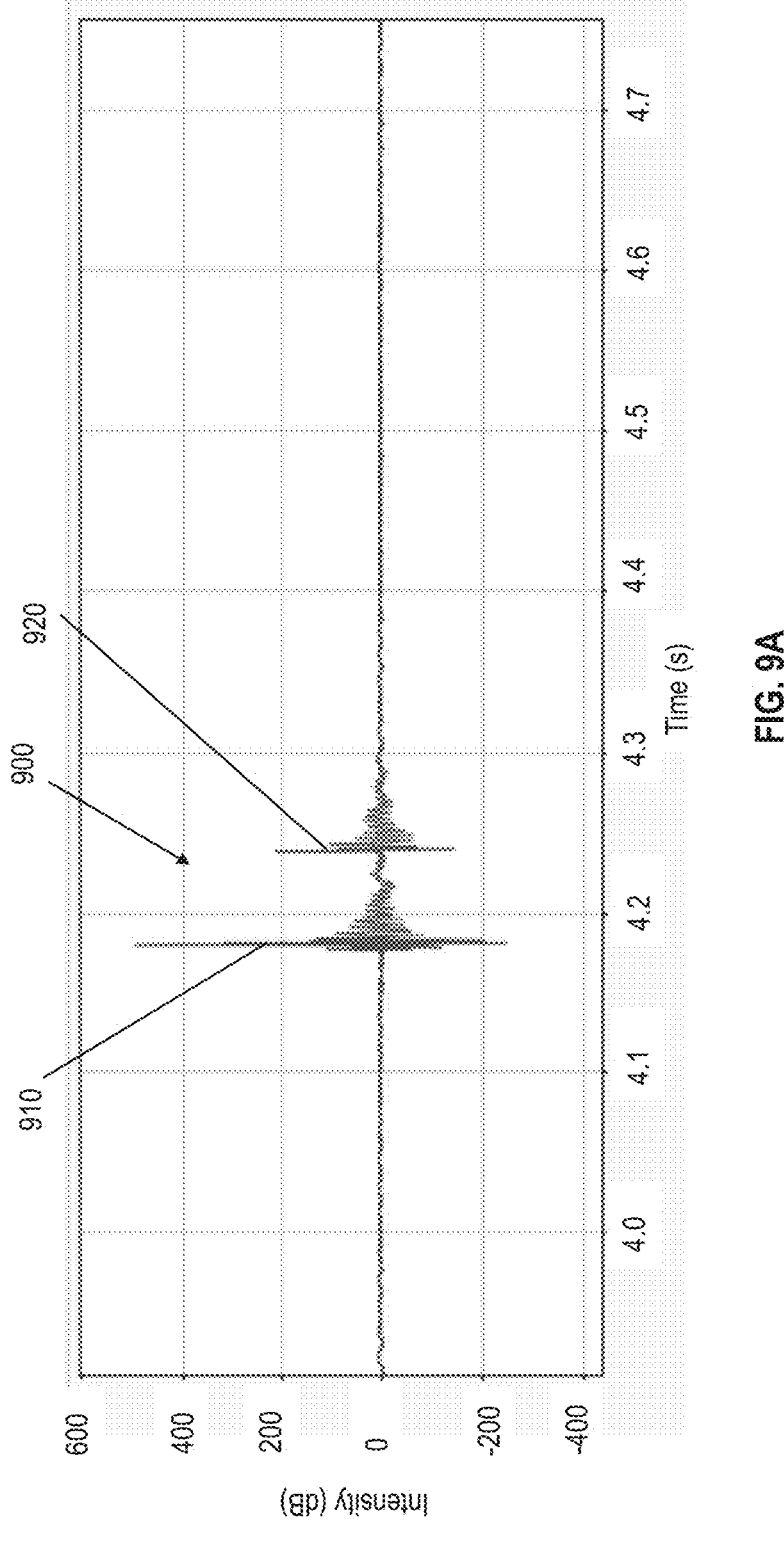
FIGS. 9A and 9B are exemplary vibration signature graphs of discrete and continuous interactions, respectively, in accordance with the present disclosure.

Referring to FIG. 9A, a graph 900 of vibration intensity (of any suitable units) over time representing a vibration signature for a discrete interaction between relatively movable components such as a pick initially contacting a tooth, as indicated at 910, and subsequently releasing from the tooth, as indicated at 920, is shown. Graph 900 may represent, for example, the interaction between pick 833 of first component 832 with one of the teeth 835 of second component 834 (see FIG. 6A). However, graph 900 is provided only for exemplary purposes to illustrate a type of vibration signature capable of being detected based on a discrete interaction between components, e.g., a pick and tooth, and, thus, the particular units and/or values in graph 900 are not of importance. In use, a vibration signature may be based on a plurality of discrete interactions that may be similar or different from one another and similarly or differently spaced-apart.

Figure 9B:
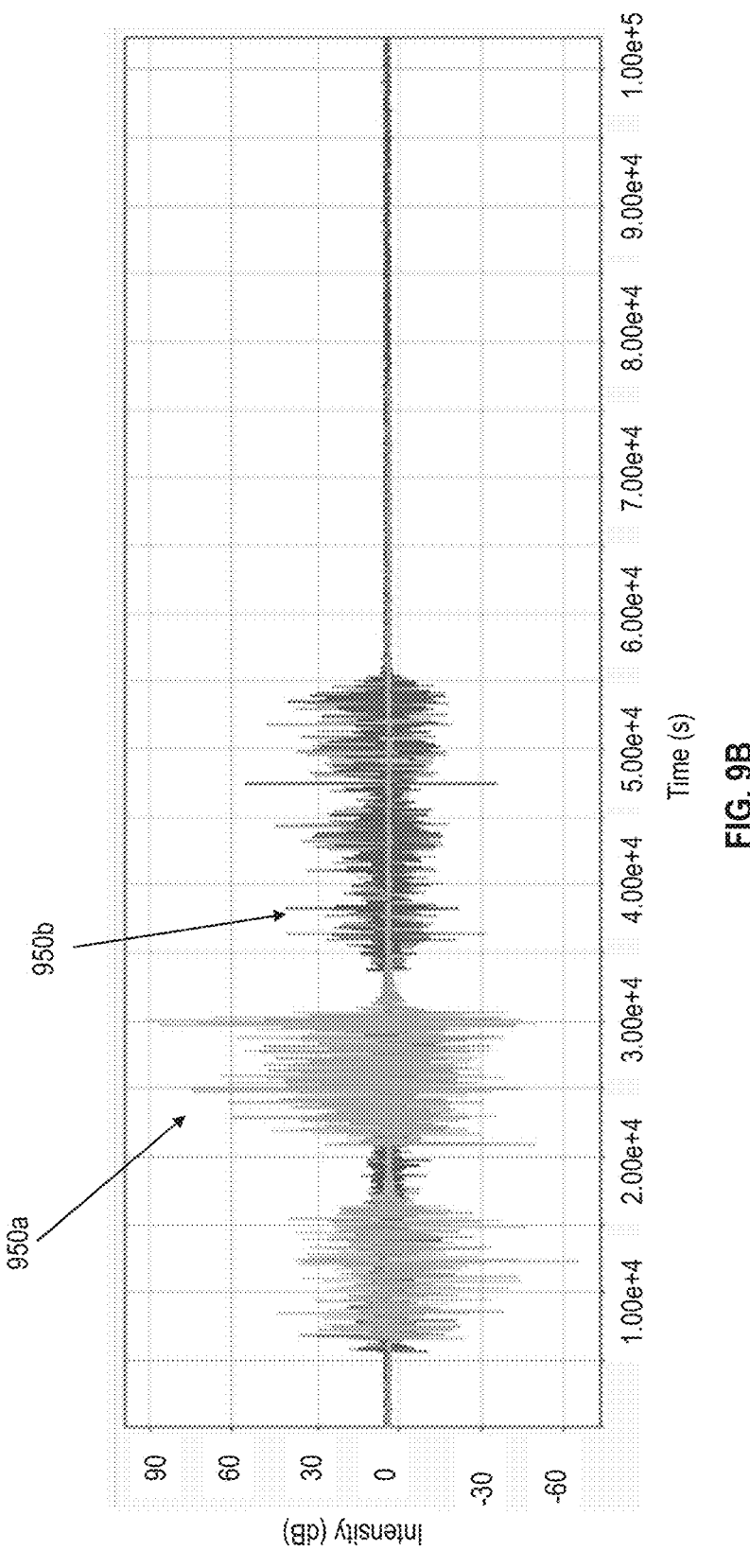

Turning to FIG. 9B, first and second graphs 950a, 950b of vibration intensity over time representing vibration signatures for continuous interactions between components such as frictionally sliding surfaces are shown. Graphs 950a, 950b may represent, for example, the interaction between surfaces 853, 855 of first and second components 852, 854 (see FIG. 6C), respectively, moving at different speeds. As with graph 900 (FIG. 9A), graphs 950a, 950b are provided only for exemplary purposes to illustrate types of vibration signatures capable of being detected based on a continuous interaction between components, e.g., frictionally sliding surfaces, and, thus, the particular units and/or values in graphs 950a, 950b are not of importance. Further, a particular signature need not be based on either discrete or continuous interactions between components, or be limited to interactions between only two components but may include combinations of discrete and continuous interactions and/or interactions between three or more components and/or multiple pairs, trios, etc. of components.

It should be understood that various aspects disclosed herein may be combined in different combinations than the combinations specifically presented hereinabove and in the accompanying drawings. In addition, while certain aspects of the present disclosure are described as being performed by a single module or unit for purposes of clarity, it should be understood that the techniques of this disclosure may be performed by a combination of units or modules associated with, for example, a surgical system.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structures or any other physical structure suitable for implementation of the described techniques. Also, the techniques could be fully implemented in one or more circuits or logic elements.

While several implementations of the disclosure are shown in the drawings and described herein, it is not intended that the disclosure be limited thereto, as it is intended that the disclosure be as broad in scope as the art will allow and that the specification be read likewise. Therefore, the above description should not be construed as limiting, but merely as exemplifications of implementations. Those skilled in the art will envision other modifications within the scope and spirit of the claims appended hereto.

14

What is claimed is:

1. A surgical system, comprising:
a surgical instrument including a housing, an end effector assembly distally-spaced from the housing, and a movable component movable relative to the housing upon actuation of the movable component;
a motion sensor disposed on or within the housing, the motion sensor configured to sense a vibration signature associated with movement of the movable component relative to the housing; and
a computing device communicating with the motion sensor and configured to receive the vibration signature therefrom, the computing device configured to determine a condition of the movable component based on the vibration signature; the condition of the movable component comprising at least one of: an amount of movement of the movable component, a direction of movement of the movable component, a speed of movement of the movable component, or an acceleration of movement of the movable component.

2. The surgical system according to claim 1, wherein the surgical instrument further includes an amplification mechanism coupled to the movable component and configured to produce amplified vibrations to facilitate sensing the vibration signature.

3. The surgical system according to claim 2, wherein the amplification mechanism includes at least one of a discrete amplifier or a continuous amplifier.

4. The surgical system according to claim 1, wherein the movable component is configured to translate relative to the housing upon actuation of the movable component.

5. The surgical system according to claim 1, wherein the movable component is manually actuated.

6. The surgical system according to claim 1, wherein the movable component is actuated by a powered input.

7. The surgical system according to claim 6, wherein the powered input is a surgical robot.

8. The surgical system according to claim 1, wherein the motion sensor is removably attachable to the housing.

9. The surgical system according to claim 1, further comprising a surgical generator connected to the surgical instrument and configured to transmit energy to the end effector assembly for treating tissue therewith.

10. The surgical system according to claim 9, wherein the computing device is part of the surgical generator.

11. The surgical system according to claim 1, wherein the motion sensor includes an accelerometer.

12. A method of monitoring a surgical instrument, comprising:
sensing a vibration signature generated from movement of a movable component of a surgical instrument relative to a housing of the surgical instrument; and
determining, based on the sensed vibration signature, a condition of the movable component by determining at least one of: an amount of movement of the movable component, a direction of movement of the movable component, a speed of movement of the movable component, or an acceleration of movement of the movable component.

13. The method according to claim 12, wherein sensing the vibration signature includes sensing amplified vibrations produced by an amplification mechanism coupled to the movable component.

14. The method according to claim 13, wherein sensing the amplified vibrations includes at least one of sensing discrete amplified vibrations or continuous amplified vibrations.

15. The method according to claim 12, further comprising determining a condition of an end effector assembly of the surgical instrument based on the determined condition of the movable component.

16. The method according to claim 12, wherein determining the condition of the movable component includes running at least one machine learning algorithm.

17. The method according to claim 12, wherein determining the condition of the movable component includes comparative analysis.

18. The method according to claim 12, wherein the vibration signature is sensed by a motion sensor releasably attached to the surgical instrument.

* * * * *